(12) United States Patent
Michaels et al.

(10) Patent No.: US 8,333,474 B2
(45) Date of Patent: Dec. 18, 2012

(54) OPTICAL INSTRUMENT ALIGNMENT SYSTEM

(75) Inventors: Richard J. Michaels, Irvine, CA (US); Max Hall, Corona, CA (US); Diego Cueto, Monarch Beach, CA (US); T. Scott Rowe, Dana Point, CA (US); Thomas Padrick, Seattle, WA (US)

(73) Assignee: WaveTec Vision Systems, Inc., Aliso Viejo, CA (US)

( * ) Notice: Subject to any disclaimer, the term of this patent is extended or adjusted under 35 U.S.C. 154(b) by 254 days.

(21) Appl. No.: 12/206,974

(22) Filed: Sep. 9, 2008

(65) Prior Publication Data
US 2009/0103050 A1   Apr. 23, 2009

Related U.S. Application Data

(60) Provisional application No. 61/038,386, filed on Mar. 20, 2008, provisional application No. 61/012,366, filed on Dec. 7, 2007, provisional application No. 60/981,146, filed on Oct. 19, 2007.

(51) Int. Cl.
*A61B 3/14* (2006.01)
(52) U.S. Cl. .................... 351/208; 351/246; 351/205
(58) Field of Classification Search ............... 351/200, 351/206, 205, 208, 246
See application file for complete search history.

(56) References Cited

U.S. PATENT DOCUMENTS

| | | |
|---|---|---|
| 4,125,320 A | 11/1978 | Rassow |
| 4,173,398 A | 11/1979 | Okamoto et al. |
| 4,293,198 A | 10/1981 | Kohayakawa et al. |
| 4,353,625 A | 10/1982 | Nohda et al. |
| 4,372,655 A | 2/1983 | Matsumura et al. |
| 4,376,573 A | 3/1983 | Matsumura et al. |
| 4,390,255 A | 6/1983 | Nohda et al. |
| 4,421,391 A | 12/1983 | Matsumura et al. |
| 4,459,027 A | 7/1984 | Kafri et al. |
| 4,541,697 A | 9/1985 | Remijan |
| 4,640,596 A | 2/1987 | Humphrey |
| 4,650,301 A | 3/1987 | Humphrey |
| 4,669,835 A | 6/1987 | Humphrey |

(Continued)

FOREIGN PATENT DOCUMENTS

EP   0931504 A1   7/1999
(Continued)

OTHER PUBLICATIONS

Search Report for PCT Application No. PCT/US2008/080153, Dated Jan. 23, 2009.
(Continued)

*Primary Examiner* — James Greece
(74) *Attorney, Agent, or Firm* — Knobbe, Martens, Olson and Bear, LLP

(57) ABSTRACT

An ophthalmic apparatus for precisely positioning an optical instrument, such as a wavefront aberrometer, in three dimensions with respect to a patient's eye. The ophthalmic apparatus may include an optical instrument directed in a first direction toward a target area to receive light therefrom and a camera directed in a second direction toward the target area to receive light therefrom, the first and second directions being non-parallel. The camera may include imaging optics to form an optical image on a photodetector array using light reflected from the target area. The ophthalmic apparatus may also include a processor configured to correlate a position of the optical image on the photodetector array with the distance between the optical instrument and the target area.

33 Claims, 8 Drawing Sheets

U.S. PATENT DOCUMENTS

| | | | |
|---|---|---|---|
| 4,692,003 A | 9/1987 | Adachi et al. | |
| 4,721,379 A | 1/1988 | L'Esperance | |
| 4,730,917 A | 3/1988 | Krueger | |
| 4,964,715 A | 10/1990 | Richards | |
| 4,984,883 A | 1/1991 | Winocur | |
| 5,080,477 A | 1/1992 | Adachi | |
| 5,157,427 A | 10/1992 | Humphrey | |
| 5,164,750 A | 11/1992 | Adachi | |
| 5,206,672 A | 4/1993 | Rowe | |
| 5,208,619 A | 5/1993 | Campbell | |
| 5,223,863 A | 6/1993 | Heine | |
| 5,252,999 A | 10/1993 | Sukigara | |
| 5,258,791 A | 11/1993 | Penny et al. | |
| 5,270,749 A | 12/1993 | Okamura | |
| 5,307,097 A | 4/1994 | Baker | |
| 5,374,193 A | 12/1994 | Trachtman | |
| 5,576,780 A | 11/1996 | Yancey | |
| 5,909,268 A | 6/1999 | Isogai et al. | |
| 5,936,706 A | 8/1999 | Takagi | |
| 5,949,521 A | 9/1999 | Williams et al. | |
| 5,963,300 A | 10/1999 | Horwitz | |
| 5,994,687 A | 11/1999 | Chanteloup et al. | |
| 6,002,484 A | 12/1999 | Rozema et al. | |
| 6,007,204 A | 12/1999 | Fahrenkrug et al. | |
| 6,022,108 A * | 2/2000 | Yoshida et al. | 351/208 |
| 6,043,885 A | 3/2000 | Mazuet et al. | |
| 6,050,687 A | 4/2000 | Bille et al. | |
| 6,095,651 A | 8/2000 | Williams et al. | |
| 6,155,684 A | 12/2000 | Bille et al. | |
| 6,199,986 B1 | 3/2001 | Williams et al. | |
| 6,264,328 B1 | 7/2001 | Williams et al. | |
| 6,270,221 B1 | 8/2001 | Liang et al. | |
| 6,271,915 B1 | 8/2001 | Frey et al. | |
| 6,275,718 B1 | 8/2001 | Lempert | |
| 6,382,794 B1 | 5/2002 | Lai et al. | |
| 6,409,345 B1 | 6/2002 | Molebny et al. | |
| 6,439,720 B1 | 8/2002 | Graves et al. | |
| 6,460,997 B1 | 10/2002 | Frey et al. | |
| 6,497,483 B2 | 12/2002 | Frey et al. | |
| 6,550,917 B1 | 4/2003 | Neal et al. | |
| 6,572,230 B2 | 6/2003 | Levine | |
| 6,588,902 B2 | 7/2003 | Isogai | |
| 6,609,794 B2 | 8/2003 | Levine | |
| 6,626,535 B2 | 9/2003 | Altmann | |
| 6,736,509 B2 | 5/2004 | Martino et al. | |
| 6,736,510 B1 | 5/2004 | Van Heugten | |
| 6,781,681 B2 | 8/2004 | Horwitz | |
| 6,908,196 B2 | 6/2005 | Herekar et al. | |
| 6,926,710 B2 | 8/2005 | Cox et al. | |
| 6,997,555 B2 | 2/2006 | Dick et al. | |
| 7,034,949 B2 | 4/2006 | Horwitz | |
| 7,057,806 B2 | 6/2006 | Atkinson | |
| 7,303,281 B2 | 12/2007 | Wakil et al. | |
| 7,336,371 B1 | 2/2008 | Haidner et al. | |
| 7,341,348 B2 | 3/2008 | Eagan | |
| 7,350,920 B2 | 4/2008 | Levine | |
| 7,556,378 B1 | 7/2009 | Ianchulev | |
| 7,878,655 B2 | 2/2011 | Salvati et al. | |
| 2002/0082629 A1 | 6/2002 | Cox et al. | |
| 2002/0118349 A1 | 8/2002 | Yang et al. | |
| 2002/0163623 A1 | 11/2002 | Hirohara et al. | |
| 2003/0058403 A1* | 3/2003 | Lai et al. | 351/212 |
| 2003/0174281 A1 | 9/2003 | Herekar et al. | |
| 2004/0263785 A1 | 12/2004 | Chernyak | |
| 2005/0203422 A1 | 9/2005 | Wei | |
| 2005/0243276 A1 | 11/2005 | Van Heugten et al. | |
| 2005/0278004 A1 | 12/2005 | Steinert et al. | |
| 2008/0004610 A1 | 1/2008 | Miller et al. | |
| 2008/0088795 A1 | 4/2008 | Goldstein et al. | |
| 2008/0192201 A1* | 8/2008 | Wengler | 351/205 |
| 2008/0291396 A1 | 11/2008 | Baer et al. | |
| 2009/0164007 A1 | 6/2009 | Van Heugten | |

FOREIGN PATENT DOCUMENTS

| | | |
|---|---|---|
| JP | 01-308552 | 12/1989 |
| WO | WO 92/01417 | 2/1993 |
| WO | WO 96/22506 | 7/1996 |
| WO | WO 01/26591 A1 | 4/2001 |
| WO | WO 01/58339 | 8/2001 |
| WO | WO 03/050472 A1 | 6/2003 |
| WO | WO 2004/093663 A2 | 11/2004 |
| WO | WO 2006/081031 A2 | 8/2006 |

OTHER PUBLICATIONS

Straub et al., "Design of a compact Shack-Hartmann aberrometer for real-time measurement of aberrations in human eyes," 2000 Optical Society of America, pp. 110-113.

Gupta, et al., "Design and use of an infrared Pupilometer for real-time pupil mapping in response to incremental illumination levels," 2000 Optical Society of America, Total 4 pages.

Quiroga, et al., "Fourier transform method for automatic processing of moire deflectograms," Jun. 1999, Society of Photo-Optical Instrumentation Engineers, pp. 974-982.

Rosales et al., "Phakometry and lens tilt and decentration using a custom-developed Purkinje imaging apparatus: validation and measurements," Journal of the Optical Society of America, vol. 23, No. 3, Mar. 2006, pp. 509-520.

Castro et al., "Tilt and decentration of intraocular lenses in vivo from Purkinje and Scheimpflug imaging: Validation study," J. Cataract Refract. Surg. 2007; 33:418-429.

Tabernero et al., "Instrument for measuring the misalignments of ocular surfaces," Optical Society of America, Oct. 30, 2006, vol. 14, No. 22.

Uozato et al., "Intraoperative Confirmation Device for IOL Centering," Folia Ophthalmologica Japonica, vol. 41, 1990, pp. 1325-1329.

Non-Final Office Action issued on Oct. 5, 2012 in U.S. Appl. No. 12/835,665.

* cited by examiner

OPTICAL INSTRUMENT ALIGNMENT SYSTEM

CROSS-REFERENCE TO RELATED APPLICATIONS

This application claims priority to U.S. Provisional Patent Application 60/981,146, filed on Oct. 19, 2007 and entitled "METHOD AND SYSTEM FOR OPHTHALMOLOGIC WAVEFRONT MEASUREMENT," and to U.S. Provisional Patent Application 61/012,366, filed on Dec. 7, 2007 and entitled "ACCURATE FOCUS TECHNIQUE FOR AN INTRAOPERATIVE WAVEFRONT ANALYZER," and to U.S. Provisional Patent Application 61/038,386, filed on Mar. 20, 2008 and entitled "OPTICAL INSTRUMENT ALIGNMENT SYSTEM," each of which is hereby incorporated by reference herein in its entirety.

BACKGROUND OF THE INVENTION

1. Field of the Invention

Embodiments of the invention generally relate to systems and methods for aligning an optical instrument at a desired spatial position relative to a target location such as, for example, the corneal apex of a human eye.

2. Description of the Related Art

Refractive surgery and other corrective procedures are commonly performed on the human eye. Such refractive surgical procedures are performed to improve the vision of the patient by altering select refractive properties of the eye (e.g., changing the curvature of the cornea, replacing select parts of the natural eye, such as the lens or the cornea, or by adding additional refractive elements to the eye). The surgeon's goal is to generally improve the overall vision of the patient as compared to the patient's pre-surgical visual state.

As part of the procedure, refractive measurements of the patient's eye are taken, usually both before and after surgery. A number of different devices currently exist by which the refractive measurements may be taken, such as wavefront aberrometers, phoroptors, corneal topographers, autorefractors, and keratometers. Of these, wavefront aberrometers generally provide the greatest detail about the refractive properties of the eye.

One important issue faced by many medical diagnosis optical systems is determining and/or maintaining a precise spatial relationship between the portion of the body undergoing diagnosis and the optical instrument. This is particularly true in the case of optical instruments, such as wavefront aberrometers, designed for measurement of properties of the eye. In many circumstances, determining a precise spatial relationship between the wavefront aberrometer and the eye allows for improved accuracy and precision in measurements performed by the wavefront aberrometer.

SUMMARY OF THE INVENTION

In some embodiments, an ophthalmic apparatus comprises: an optical instrument directed in a first direction toward a target area to receive light therefrom; a camera directed in a second direction toward the target area to receive light therefrom, the camera comprising imaging optics and a photo-sensitive element, wherein the first and second directions are non-parallel and wherein the imaging optics form an optical image on the photo-sensitive element using light reflected from the target area; and a processor configured to correlate a position of the optical image on the photo-sensitive element with the distance between the optical instrument and the target area.

In some embodiments, an ophthalmic apparatus comprises: an optical instrument having a first set of optics configured to receive light from the eye of a patient along a first optical axis defined by the first set of optics; and a system for positioning the optical instrument at a desired position relative to the eye in an x-y-z three-dimensional coordinate system, the desired position comprising x, y, and z coordinates, the positioning system comprising a photodetector and being calibrated to define a reference location on the photodetector, the reference location on the photodetector being determined based at least in part on the corneal curvature of the eye and on the desired position relative to the eye, the apparatus being configured such that a spatial relationship between at least one optical indicia and the reference location on the photodetector varies as the apparatus is moved relative to the eye to provide positioning information for positioning the instrument at the desired position, the optical indicia comprising light reflected from the eye to the photodetector along a second optical axis, different from the first.

In some embodiments, a method of using an ophthalmic apparatus comprises: providing an optical instrument to perform a diagnostic measurement on the eye of a patient; providing a system for positioning the optical instrument at a desired position relative to the eye in an x-y-z three-dimensional coordinate system, the positioning system comprising a photodetector; providing curvature data about the corneal curvature of the patient's eye; causing light to be reflected from the cornea of the eye such that it impinges upon the photodetector at one or more locations; and moving the optical instrument in x, y, and z directions to position the optical instrument at the desired position relative to the eye based at least in part upon the curvature data and upon the one or more locations on the photodetector.

In some embodiments, an ophthalmic apparatus comprises: an optical instrument having a first set of optics that define a first optical axis; and a positioning system coupled to the optical instrument, the positioning system comprising: a second set of optics that define a second optical axis, the first and second optical axes being directed at a common target area and being non-parallel at the target area; a photodetector array positioned to receive light propagating along the second optical axis; an optical image on the photodetector array comprising light reflected from the target area through the second set of optics to one or more locations on the photodetector array; and a processor configured to correlate the one or more locations of the optical image on the photodetector array with the distance between the optical instrument and the target area along the first optical axis.

DETAILED DESCRIPTION OF THE PREFERRED EMBODIMENT

Figure 1:
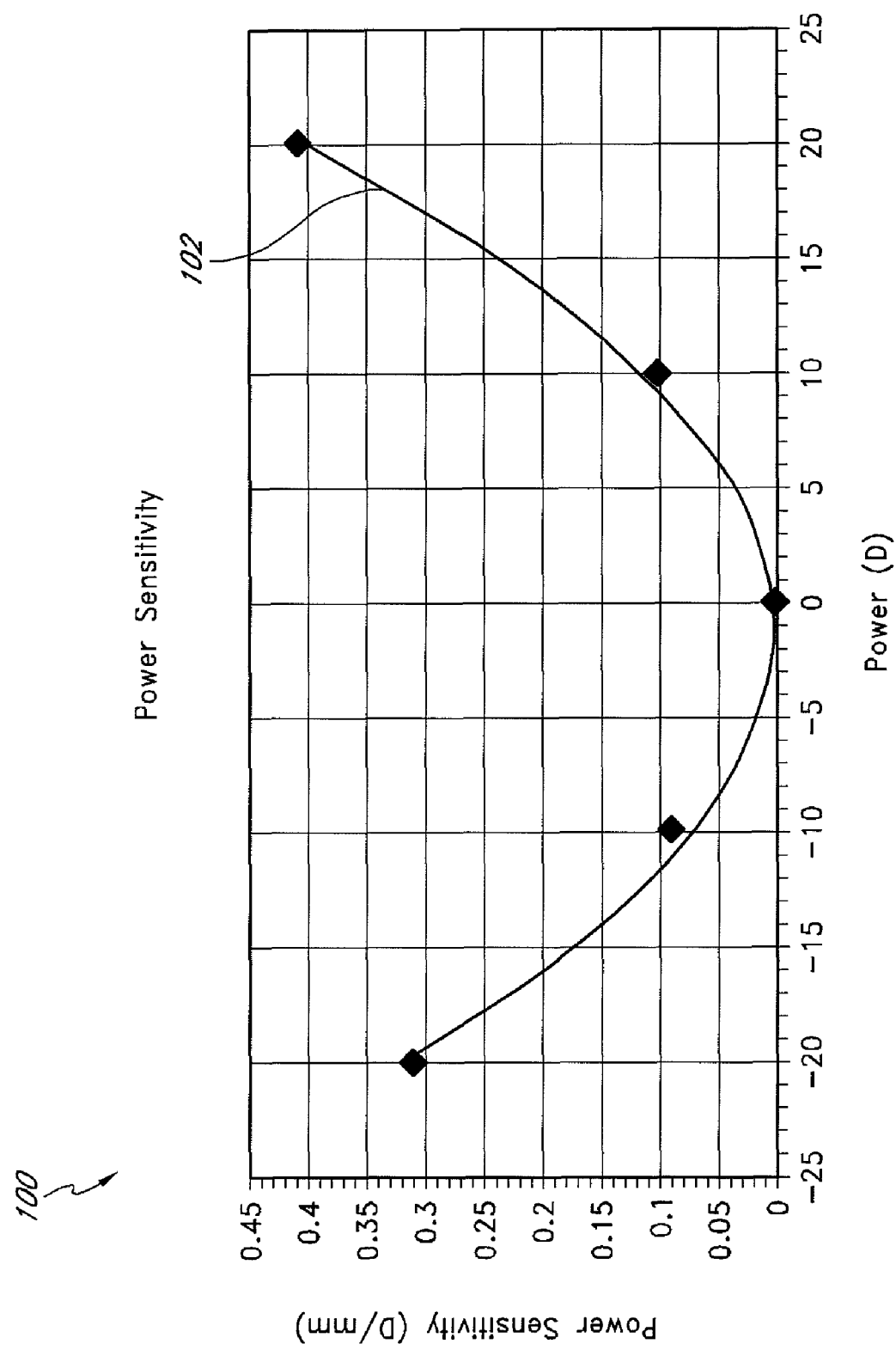
FIG. 1 is a graph that illustrates the sensitivity of refractive optical power measurements with respect to errors in the longitudinal position of a wavefront aberrometer.

Intraocular lens (IOL) implantation surgery is one of several ophthalmic procedures that involve measurements of the refractive power of a patient's eye. In a typical IOL implantation procedure, a surgeon removes a patient's natural crystalline lens from the eye. Upon removal of the natural lens, the surgeon may take a measurement to determine the optical power of the appropriate IOL implant that will restore the eye to an emmetropic condition. This has traditionally been done by measuring preoperatively the axial length of the patient's eye using, for example, an ultrasound device and also by measuring the corneal curvature. However, in some embodiments described herein, the optical power of the appropriate IOL implant that will restore the eye to an emmetropic condition is found by direct measurement of the aphakic refractive power of the patient's eye. This refractive power measurement can be taken with any of several optical instruments, including, for example, a wavefront aberrometer comprising a Talbot-Moire interferometer. Once this measurement is performed and the proper refractive power of the IOL implant is determined, the surgeon inserts the IOL implant in the patient's eye in place of the removed natural crystalline lens.

The wavefront aberrometer should be precisely laterally centered with respect to the corneal apex, or vertex, of the patient's eye in order to achieve the most accurate measurements. For example, proper lateral centration of the wavefront aberrometer may be achieved when the optical axis of the aberrometer is coincident with the visual axis of the patient's eye. The wavefront aberrometer should also be positioned at a precise longitudinal position, or depth, along the optical axis of the aberrometer, from the corneal apex. Proper longitudinal positioning ensures that the focus of the wavefront aberrometer is accurately located with respect to the patient's corneal apex. For convenience, a three-dimensional coordinate system can be defined having a z-axis parallel with the visual axis of the patient's eye, and x- and y-axes that are mutually orthogonal to the z-axis and that define a plane perpendicular to the visual axis of the eye. In the context of such a three-dimensional coordinate system, lateral positioning corresponds to the x and y coordinates of the wavefront aberrometer, while longitudinal positioning corresponds to its z coordinate.

Measurements obtained with the wavefront aberrometer are used as inputs to an IOL power calculation. IOL power calculations assume that the refractive power measurements were taken at the corneal vertex plane, thus the importance of proper longitudinal positioning of the aberrometer with respect to the corneal vertex. Longitudinal, or depth, alignment errors reduce the accuracy of the refractive power readings taken by the wavefront aberrometer, resulting in the selection of an IOL implant with incorrect refractive power and, consequently, suboptimal surgical outcomes. However, data concerning the longitudinal positioning of the aberrometer during the capture of a series of refractive measurements can be used to perform vertex correction calculations that correct the position of the measurement at the corneal plane to improve the accuracy of the IOL power calculation and, hence, surgical outcomes for patients for each of a series of measurements.

FIG. 1 is a graph 100 that illustrates the sensitivity of refractive optical power measurements with respect to longitudinal errors in the positioning of a wavefront aberrometer. The sensitivity of optical power measurements with respect to longitudinal alignment error is illustrated by curve 102. This sensitivity is plotted as a function of the optical power enhancement that is needed to restore a patient's aphakic eye to an emmetropic condition.

A normal aphakic eye is hyperopic. For example, the refractive power of a typical aphakic human eye is about +13 diopters (D). Therefore, the abscissa coordinate of a point on curve 102 is commonly approximately +13 D for a typical patient undergoing IOL implantation surgery but can vary up to as much as +25 D. As discussed previously, the accuracy of the aphakic measurement to determine the proper optical power of the IOL implant varies with errors in the lateral and longitudinal position of the aberrometer with respect to the eye.

For the point along curve 102 having an abscissa coordinate of +13 D, the sensitivity of the measurement is approximately 0.18 D of error for every 1 mm of longitudinal alignment error. In a very hyperopic aphakic eye, the sensitivity of the refractive power measurement can reach 0.4 D of error for every 1 mm of longitudinal alignment error, or higher. As shown by curve 102, the more hyperopic the aphakic eye, the greater the sensitivity of the refractive power measurement to longitudinal alignment errors. Longitudinal errors in the positioning of the wavefront aberrometer that are greater than about ±0.15 mm can result in unacceptable errors in the refractive optical power measurements that are used to select an IOL implant. While lateral alignment errors in the position of a wavefront aberrometer with respect to an eye also result in inaccurate refractive power measurements, the greater technical challenge has been the development of alignment systems that reduce longitudinal positioning errors to within an acceptable range.

Figure 2:
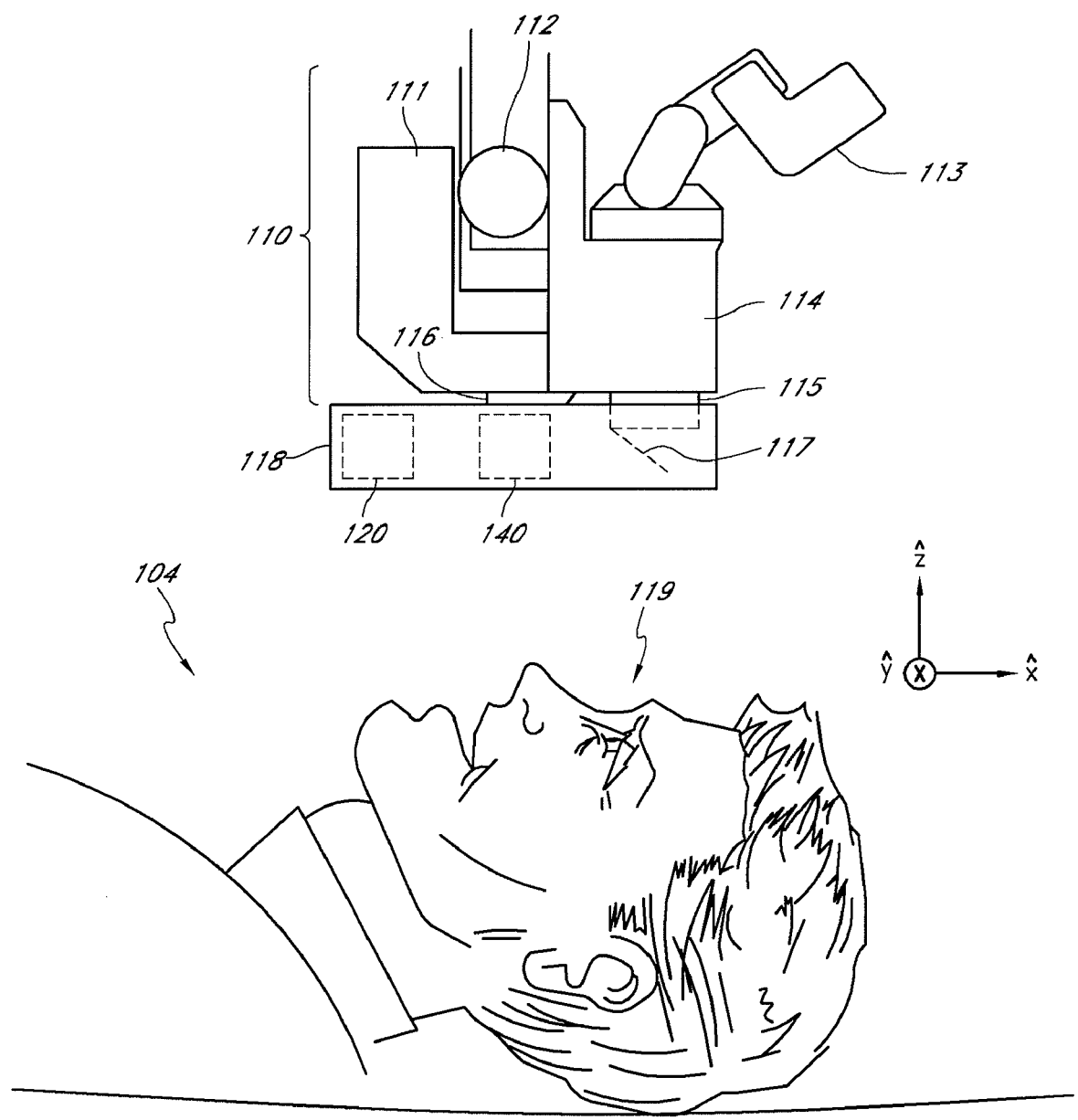
FIG. 2 schematically illustrates an embodiment of an optical instrument (e.g., a wavefront aberrometer) and alignment system mounted to a surgical microscope.

FIG. 2 schematically illustrates an embodiment of an optical instrument 120 and alignment system 140 mounted to a surgical microscope 110. The surgical microscope 110 has an optical instrument/alignment system module 118 rigidly affixed thereto. The module 118 includes the optical instrument 120 (e.g., a wavefront aberrometer) and the alignment system 140, as described herein. The optical instrument 120 is intended to represent any optical instrument for which it is desirable to establish and/or maintain a precise three-dimensional spatial relationship between the instrument and a target location 119, such as, for example, the corneal apex of an eye of a patient 104. The target location 119 can also be any other region, whether on the eye or some other body part, which is the subject of a treatment or measurement being performed by the optical instrument 120.

In some embodiments, the optical instrument 120 is a wavefront aberrometer. In other embodiments, the optical instrument 120 is an autorefractor, a keratometer, a corneal topographer, or an Optical Coherence Tomographer (OCT), for example. While the optical instrument 120 and the alignment system 140 are illustrated as a single module 118 in FIG. 2, it should be appreciated that the optical instrument 120 and the alignment system 140 could also be separate modules. In some embodiments, the optical instrument 120 and the alignment system 140 are rigidly mechanically coupled to one another. Moreover, the optical instrument 120 and the alignment system 140 could be arranged differently than is illustrated in FIG. 2.

In the embodiment illustrated in FIG. 2, the surgical microscope 110 includes an eyepiece 113 that allows a surgeon to view a region encompassing the target location 119 of the optical instrument 120. The eyepiece 113 may be binocular or monocular, as preferred by the surgeon. The surgeon may use the surgical microscope 110 to coarsely position the optical instrument 120 at a desired position relative to the target location 119 before using the alignment system 140 to more accurately position the optical instrument 120, as described herein. For example, the surgeon may view the target location 119 through the eyepiece 113 and roughly align the optical instrument 120 with respect to, for example, a patient's corneal apex. This can be done manually or with actuators (not shown) and actuator controls (e.g., foot switches). For example, the surgical microscope 110 can be used to laterally center the optical instrument 120 over the corneal apex using a reticle provided within the microscope. The surgical microscope 110 can be used to longitudinally position the optical instrument 120 with respect to the corneal apex by using the microscope's focus controls. However, the coarse alignment that can be achieved using the surgical microscope 110 is often insufficient to achieve treatment or measurement results with the optical instrument 120 at an acceptable level of accuracy.

The surgical microscope 110 also includes a light source 111 that illuminates the target location 119, a focusing knob 112 for adjusting the focus of the microscope 110, and an objective lens 115 for collecting light from the target location 119. The surgical microscope 110 can be of any style or configuration known in the art, although, in some embodiments, some retrofitting may be required to securely affix the optical instrument/alignment system module 118 thereto. It should also be appreciated that, while a surgical microscope 110 may be helpful in achieving coarse lateral and longitudinal positioning of the optical instrument 120 with respect to the target location 119, it is not required in all embodiments. The optical instrument/alignment system module 118 may be attached to the microscope 110 in any suitable manner. As shown in FIG. 2, the module 118 is removably affixed to the surgical microscope 110 by one or more fasteners 116 on the body 114 of the surgical microscope 110.

In some embodiments, the optical instrument 120 operates using light of non-visible wavelengths. Thus, the optical instrument/alignment system module 118 also includes a wavelength selective mirror 117 that passes visible light to the objective lens 115 while reflecting light used by the optical instrument 120, which may be, for example, in the near infrared range, to the optical instrument 120 enclosed within the module 118. It should be appreciated that many other configurations for the optical instrument 120, alignment system 140, and surgical microscope 110, or sub-combinations thereof, are possible. Some embodiments may include additional, fewer, and/or different optical components such as mirrors, lenses, beam splitters, filters, etc. for routing light to and among these components.

Figure 3:
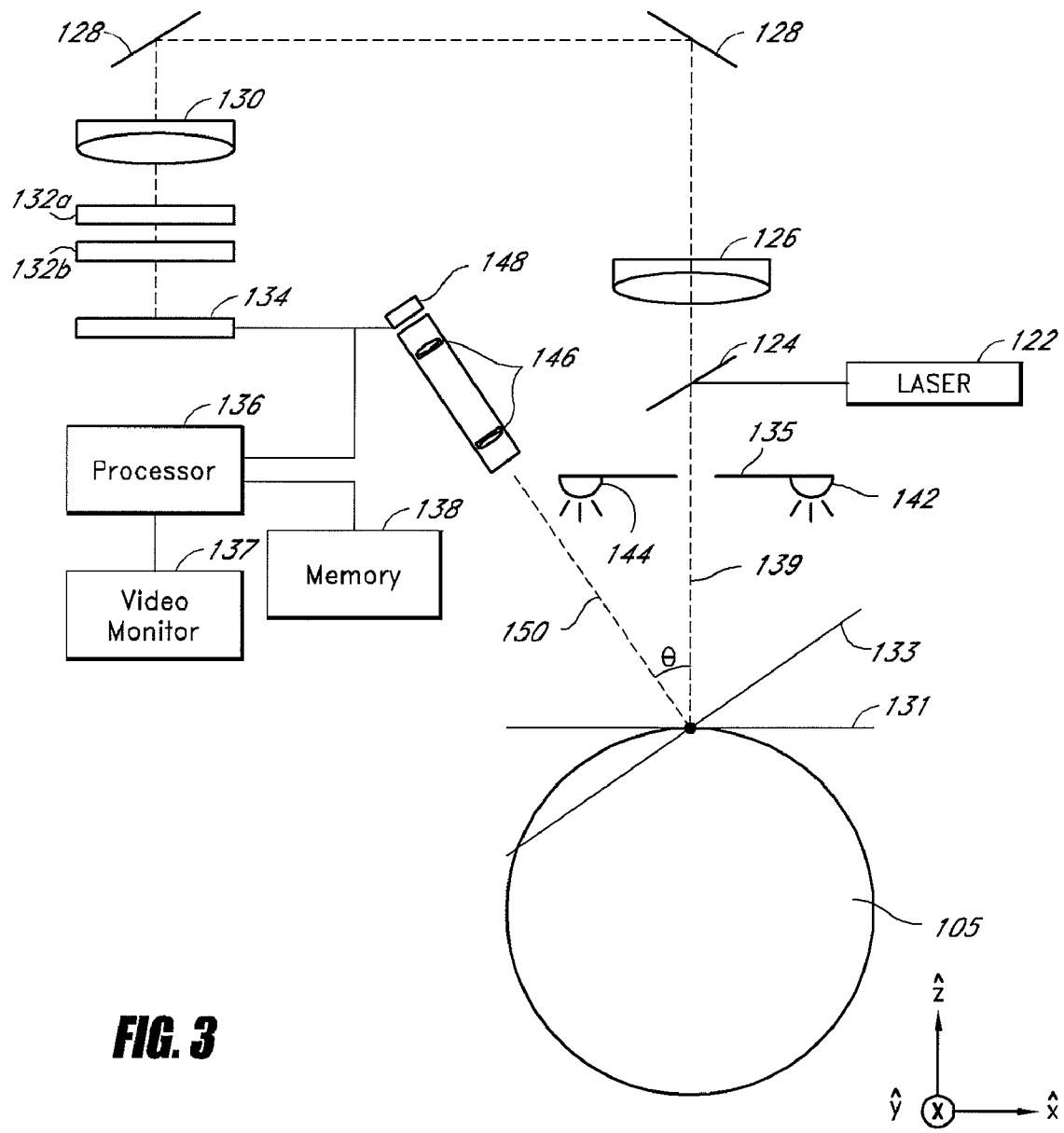
FIG. 3 schematically illustrates an embodiment of a wavefront aberrometer and an alignment system for positioning the wavefront aberrometer at a desired location relative to a target location.

FIG. 3 schematically illustrates the optical instrument 120 and the alignment system 140 that are included in the module 118 of FIG. 2. In the embodiment illustrated in FIG. 3, the optical instrument 120 is a wavefront aberrometer and is positioned above a patient's eye 105.

The wavefront aberrometer 120 includes a laser 122 that generates a thin beam of light having a planar wavefront which is directed by a beam splitter 124, toward the patient's eye 105. The laser light enters the patient's eye 105, passing through the cornea and the pupil, and impinges upon the retina. The laser light scatters from the retina and propagates back through the cornea to the wavelength selective mirror 117, returning to the beam splitter 124. Features of the eye, including the shape of the cornea, alter the planar wavefront of the scattered light, thus including information about the shape of the cornea and the refractive power of the eye in the altered wavefront.

The altered wavefront passes through a first lens doublet 126, is re-directed by a pair of relay mirrors 128, and then propagates through a second lens doublet 130. A pair of reticles, or gratings, 132a, 132b is disposed between the second lens 130 and the aberrometer detector 134. In some embodiments, the aberrometer detector 134 is a charge-coupled device (CCD). However, other detectors are also suitable. The reticles 132a, 132b generate fringe patterns on the aberrometer detector 134 which are detected and used to determine the shape of the altered wavefront in, for example, the manner described in U.S. Pat. No. 6,736,510, which is hereby incorporated herein by reference in its entirety. The example wavefront aberrometer 120 shown in FIG. 3 is a Talbot-Moire interferometer-type wavefront aberrometer and may include additional, fewer, and/or different optical elements as needed to suit design considerations, as will be apparent to those of skill in the art. When the wavefront aberrometer 120 is properly longitudinally positioned, the lenses 126, 130 image the corneal vertex plane 131 onto the first reticle 132a (the second reticle 132b is then imaged onto the aberrometer detector 134 with additional optics that are not illustrated). In addition, the optics (e.g., lens 126) of the wavefront aberrometer define an optical axis 139 of the wavefront aberrometer 120.

The alignment system 140 implements a triangulation method to determine the position of the wavefront aberrometer 120 with respect to the eye 105. The alignment system 140 includes one or more light sources. In some embodiments, the light sources used by the alignment system are light emitting diodes (LEDs) 142, 144 that are fixedly positioned about the optical axis of the wavefront aberrometer 120. The particular arrangement of one or more LEDs (e.g., 142, 144) about the optical axis 139 of the wavefront aberrometer 120 will be referred to herein as a constellation of LEDs 143. In some embodiments, the LEDs 142, 144 are disposed about the optical axis 139 of the wavefront aberrometer 120 near the input window 135 of the aberrometer. In particular, in some embodiments, four LEDs (e.g., 142, 144) are employed and are arranged about the optical axis 139 of the aberrometer 120 to form a square or rectangular constellation 143 about the input window 135 of the aberrometer. However, any number of LEDs can be used, including a single LED. In other embodiments, the LEDs (e.g., 142, 144) can be replaced with other visible features that can be imaged by the alignment system 140.

In some embodiments, the laser 122 operates at a different range of wavelengths than the LEDs 142, 144, though this is not required. In some embodiments, both the laser 122 and the LEDs 142, 144 operate in the near-infrared range. In practice, operational wavelengths of 785 nm for the laser 122 and 880 nm for the LEDs 142, 144 have been found to work well, though light from other portions of the electromagnetic spectrum could also be used.

The alignment system 140 also includes an alignment camera having alignment optics 146 and an alignment detector 148. The alignment optics 146 define an optical axis 150 of the alignment system 140. As illustrated in FIG. 3, an optical path from the patient's eye 105 to the input window 135 of the wavefront aberrometer 120 is at an angle θ with respect to an optical path from the patient's eye to the alignment system optics 146. In particular, the optical axis 150 of the alignment system 140 is at an angle θ with respect to the optical axis 139 of the aberrometer 120. Or equivalently, the alignment optics 146 are configured such that the plane 133 that is imaged by the alignment optics 146 intersects the focal plane 131 for the wavefront aberrometer 120 at the angle θ. In some embodiments, the optical axis 139 of the wavefront aberrometer 120 and the optical axis 150 of the alignment system 140 intersect at an angle in a range of approximately 5°-85°, although greater or lesser angles may also be used. For example, in some embodiments the angle θ is in the range of approximately 8°-45°. In some embodiments the angle θ is in the range of approximately 10°-15°.

Light emitted from the LEDs 142, 144 propagates toward the cornea of the eye 105. A portion of this light is reflected generally along the optical axis 150 of the alignment system 140 by the cornea. This light passes through the alignment camera's aperture to the alignment optics 146, which focus a virtual image of the LED constellation 143 onto the alignment detector 148, the virtual image being formed by the reflection of light from the LEDs 142, 144 at the cornea of the eye 105. In some embodiments, the alignment detector has a two-dimensional array of light-sensitive pixels such as, for example, a CCD sensor. Other types of detectors are also suitable. The alignment optics 146 may be configured to image a plane 133 that intersects plane 131 at or near the optical axis 139 of the wavefront aberrometer 120 onto the alignment detector 148. In some embodiments, the focal length of the alignment optics 146 is in the range from approximately 10 mm to approximately 40 mm, though focal lengths outside this range may also be used. It will be understood by those of skill in the art that the alignment optics 146 may include additional, fewer, and/or different optical elements as needed to achieve their intended purpose and to suit design-specific considerations.

In some embodiments, the processor 136 is programmable and electronically coupled to both the alignment detector 148 and the aberrometer detector 134. The processor 136 may be employed to receive data from both detector elements 134, 148 and to process the data as described in further detail below. The processor may also be electronically coupled to an appropriate memory 138, which can be used for storing accumulated data as well as parameters related to properties of the patient's eye 105. The processor 136 may also be coupled to a video monitor 137, or other display, so that visual alignment feedback may be provided to the surgeon. In some embodiments, the visual feedback is provided to aid the surgeon in aligning the intersection point of the focal planes 131, 133 at or near the surface of the cornea of the eye 105 and to aid the surgeon in maintaining that alignment while wavefront and/or additional alignment data are accumulated by the processor 136. In some embodiments, the processor 136, the memory 138, and the video monitor 137 are disposed externally to the optical instrument/alignment system module 118 rather than on the surgical microscope 110 due to size and weight considerations.

Figure 4:
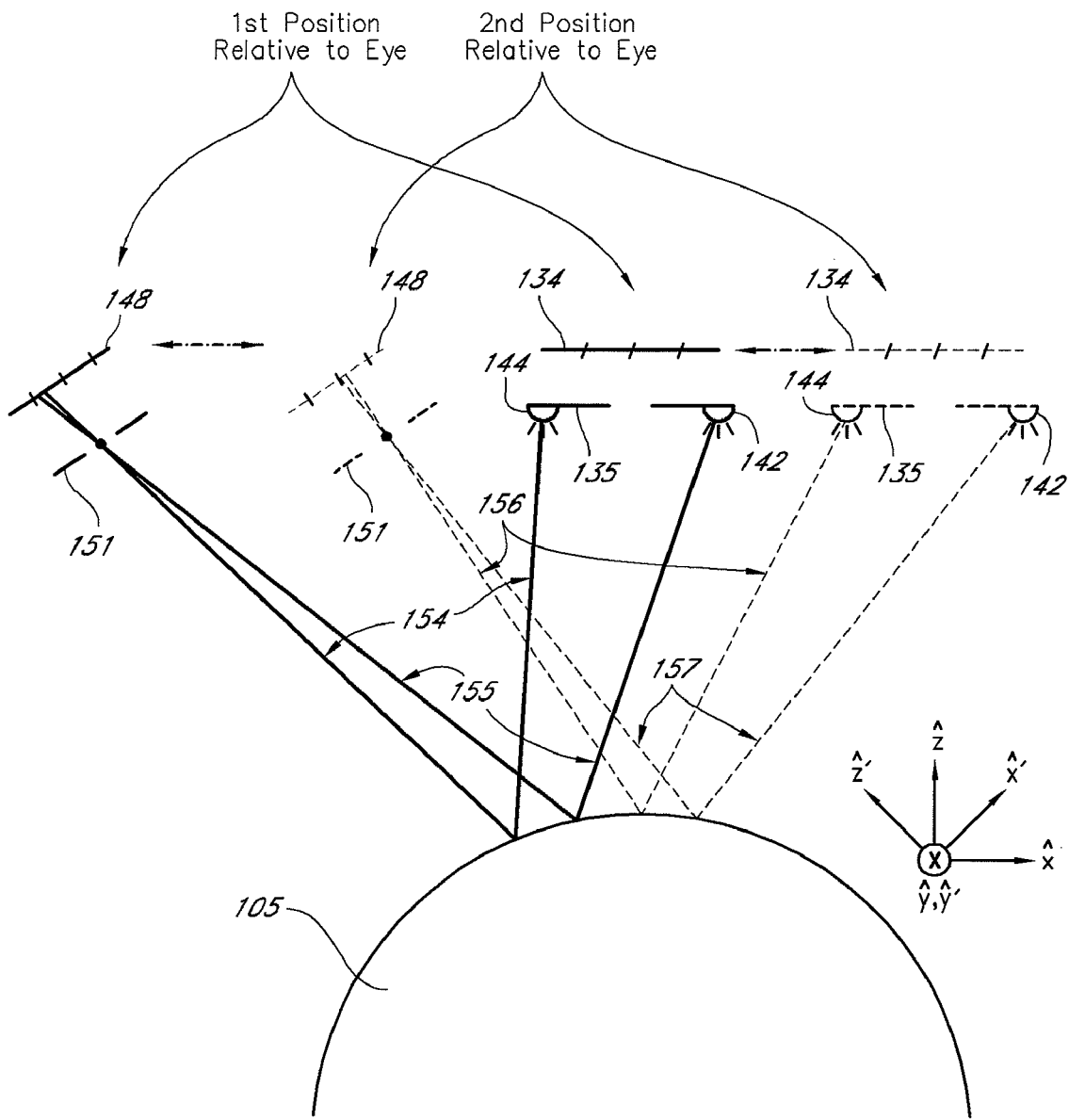
FIG. 4 schematically illustrates the translation of images of LEDs across the detector of an alignment system camera when the wavefront aberrometer is moved laterally with respect to the eye.

A first, x-y-z three-dimensional coordinate system is illustrated in FIG. 3. The z-axis of the three dimensional coordinate system is aligned with the optical axis 139 of the wavefront aberrometer 120. FIG. 4 illustrates an x-y-z-coordinate system similar to the one illustrated in FIG. 3. Motion of the wavefront aberrometer 120 in the direction of the z-axis is referred to herein as longitudinal, or depth, motion. The x-axis and the y-axis of the three-dimensional coordinate system are arranged mutually orthogonally to the z-axis. For instance, the x-axis can be aligned with the temporal axis of the patient, and the y-axis can be aligned with the superior axis of the patient. Motion of the wavefront aberrometer 120 parallel to the x-y plane is referred to herein as lateral motion. It should be understood that the three-dimensional coordinate system illustrated in FIG. 3, as well as the other figures, is for illustrative purposes only and that other coordinate systems could be used as well.

As discussed herein, it may be desirable when using certain optical instruments 120 to obtain a desired relative spatial position between the optical instrument 120 and a target location (e.g., 119) in order to achieve accurate measurement or treatment results. For instance, measurements taken by the wavefront aberrometer 120 are generally most accurate when the aberrometer 120 is laterally centered over the corneal apex of the eye 105, and the optical axis 139 of the aberrometer 120 where it intersects the eye 105 is coincident with the visual axis of the eye 105. (It should be understood that the optical axis 139 within the wavefront aberrometer 120 is not necessarily a straight line along the entire optical path within the aberrometer 120 as it may be bent by various optical elements within the aberrometer 120, such as mirrors 128. Thus, the optical axis 139 of the aberrometer may diverge from the visual axis of the eye at one or more locations within the aberrometer instrument 120.)

In addition to being laterally centered over the corneal apex of the eye 105, the wavefront aberrometer 120 should also be positioned at the proper longitudinal distance from the corneal apex in order to obtain the most accurate measurement readings. In some embodiments, the longitudinal position of the wavefront aberrometer 120 with respect to the corneal apex of the eye 105 may be measured as the distance along the optical axis 139 of the aberrometer 120 from the input window 135 to the corneal apex of the eye 105. A typical wavefront aberrometer may be designed for a working distance in the range of approximately 100 mm to approximately 500 mm, though working distances outside this range are also possible. Thus, for best measurement results, the wavefront aberrometer 120 should be positioned at a longitudinal position with respect to the corneal apex that corresponds to the working distance for which the aberrometer 120 is designed.

In some embodiments, the wavefront aberrometer 120 is located at the desired spatial position relative to the corneal apex of the eye 105 when its optics are laterally centered relative to the corneal apex and positioned at the proper working distance from the corneal apex. When this occurs, the optical axis 139 of the aberrometer 120 intersects the optical axis 150 of the of the alignment system 140 at, or near, the corneal apex of the eye 105.

As described herein, in some embodiments, the alignment system 140 outputs positioning information for moving the wavefront aberrometer 120 to the desired position with respect to the corneal apex of the eye 105. The positioning information may include, for example, data about the position of the image of the LED constellation 143 on the alignment detector 148. The positioning information may also include other data such as, for example, the spot sizes of the images of the LEDs (e.g., 142 and 144) on the alignment detector 148, and the sharpness of focus of those spots, as described herein. In some embodiments, the position of the image of the LED constellation 143 on the alignment detector 148, along with the spot sizes/sharpness of the images of the LEDs (e.g., 142 and 144), is indicative of the three-dimensional position of the wavefront aberrometer 120 relative to the corneal apex of the eye 105.

In some embodiments, the positioning information is provided to a surgeon in the form of a video signal from the alignment detector 148 to a video monitor 137, or other display, that shows the position of the image of the LED constellation 143 on the alignment detector 148 relative to a crosshair, or other reference point. The surgeon then moves the wavefront aberrometer 120 in three dimensions until the LED constellation image 143 reaches a desired spatial position relative to the crosshair. When the desired spatial position of the LED constellation relative to the crosshair is achieved, along with the simultaneous fulfillment of certain other criteria (e.g., minimal spot size of the images of the LEDs on the alignment detector 148 and high sharpness of focus of those spots), then the wavefront aberrometer 120 is positioned at the desired spatial position relative to the corneal apex of the eye 105. In other embodiments, the processor 136 is programmed to analyze the positioning information provided by the alignment system 140 and to control actuators to automatically move the wavefront aberrometer 120 to the desired position relative to the corneal apex of the eye 105.

FIG. 4 schematically illustrates the translation of the image of the LED constellation 143 across the alignment detector 148 when the wavefront aberrometer 120 is moved laterally with respect to the eye 105. FIG. 4 uses a first x-y-z-three-dimensional coordinate system similar to the one illustrated in FIG. 3. As before, motion of the wavefront aberrometer 120 in the direction of the z-axis is referred to as longitudinal, or depth, motion, while motion of the wavefront aberrometer 120 parallel to the x-y plane is referred to as lateral motion.

FIG. 4 also schematically illustrates a second, x'-y'-z' three-dimensional coordinate system. The x'-y'-z' coordinate system can be obtained by rotating the x-y-z coordinate system about the y-axis by the angle θ formed between the optical axis 139 of the wavefront aberrometer 120 and the optical axis 150 of the alignment system 140 (see e.g., FIG. 3). Thus, the z'-axis is aligned with the optical axis 150 of the alignment system 140. The y'-axis is aligned with the y-axis and the x'-axis is arranged orthogonally to both the y'-axis and the z'-axis.

FIG. 4 also includes simplified drawings of the wavefront aberrometer 120 and the alignment system 140. The simplified wavefront aberrometer 120 shows the aberrometer detector 134 and the wavefront aberrometer's input window 135, but without the imaging optics 126, the mirrors 128, 130, or the reticles 132. The simplified alignment system 140 includes two LEDs 142, 144, the alignment system's input aperture 151, and the alignment detector 148. The alignment system's imaging optics 146 are not shown for simplicity. The aberrometer detector 134 and the alignment detector 148 are illustrated at a first position relative to the eye 105 in bold, and at a second, x-y laterally displaced position relative to the eye 105 in dashed lines.

Also, in the interest of clarity, FIG. 4 does not illustrate the beam of light from the laser 122 of the wavefront aberrometer 120. Nor does FIG. 4 illustrate the movement of the laser beam spot on the aberrometer detector 134 as the wavefront aberrometer 120 is laterally displaced relative to the eye 105 in a direction parallel to the x-y plane. It should be understood, however, that if the optical axis 139 of the wavefront aberrometer 120 is aligned with the visual axis of the eye 105, the laser beam is reflected by the eye 105 back along the optical axis 139 of the aberrometer 120 to the aberrometer detector 134. As the wavefront aberrometer 120 is displaced laterally (i.e., parallel to the x-y plane), the laser beam spot likewise tracks laterally across the aberrometer detector 134.

In a somewhat like manner, x-y lateral motion of the wavefront aberrometer 120, and, consequently, x-y lateral motion of the alignment system 140 which is rigidly coupled to the aberrometer 120, causes the images of the LEDs 142, 144 to track across the alignment detector 148. The motion of the images of the LEDs 142, 144 across the alignment detector 148 is, however, parallel to the x'-y' plane since the alignment detector 148 is oriented parallel to the x'-y' plane.

The x-y lateral motion of the alignment system 140 results in x'-y' motion of the images of the LEDs 142, 144 on the alignment detector 148, at least in part, because x-y motion of the alignment system 140 has x'-y' vector components. That is, motion of the alignment system 140 in the x-direction has a vector component in the x'-direction, while motion of the alignment system 140 in the y-direction corresponds to motion in the y'-direction. Thus, x-y lateral displacement of the alignment system 140 relative to the eye 105 (as illustrated in FIG. 4), which has corresponding x'-y' vector components, causes the images of the LEDs 142, 144 to track along the alignment detector 148 parallel to the x'-y' plane for physical reasons similar to those that result in the laser beam spot of the aberrometer 120 tracking across the aberrometer detector 134 parallel to the x-y plane. In other words, the alignment detector 148 is sensitive to x-y-direction motion of the aberrometer 120 at least in part because this motion has x'-y' vector components and, thus, partially corresponds to motion that is sensed by the alignment detector 148 as lateral motion in its x'-y'-z' frame of reference. This is illustrated by the ray-traces in FIG. 4.

FIG. 4 includes ray-traces of the images of the LEDs 142, 144 that are formed on the alignment detector 148. Rays 154 and 155 correspond to the images of LEDs 142, 144 on the alignment detector 148 when the wavefront aberrometer 120 and the alignment system 140 are at the first position relative to the eye 105. Ray 154 is the chief ray of the image of LED 144 on the alignment detector 148. Ray 155 is the chief ray of the image of LED 142 on the alignment detector 148. Hash marks are included on the alignment detector 148 to better illustrate the distinct x'-y' coordinates of the images of the LEDs 142, 144 on the alignment detector 148 when the wavefront aberrometer/alignment system is at the first and second x-y lateral positions. As illustrated, the images of the LEDs 142, 144 appear on the alignment detector 148 near the left hash mark when the wavefront aberrometer 120 and the alignment system 140 are in the first position.

In a similar manner, rays 156 and 157 correspond to the images of LEDs 142, 144 on the alignment detector 148 when the wavefront aberrometer 120 and the alignment system 140 are in the second position relative to the eye 105 (illustrated with dashed lines). Ray 156 is the chief ray of the image of LED 144 on the alignment detector 148. Ray 157 is the chief ray of the image of LED 142 on the alignment detector 148. As illustrated, the images of the LEDs 142, 144 move parallel to the x'-y' plane in response to x-y lateral motion of the wavefront aberrometer/alignment system. Consequently, the images of the LEDs 142, 144 are located near the center hash mark of the alignment detector 148 when the wavefront aberrometer 120 and the alignment system 140 are at the second x-y lateral position. In this way, the location of the image of the LED constellation 143 on the alignment detector 148 provides information about the x and y coordinates of the wavefront aberrometer 120 with respect to the patient's eye 105. This information about the x and y coordinates of the wavefront aberrometer 120 can be used during coarse alignment of the aberrometer 120 with respect to the patient's eye 105, as described herein.

Figure 5:
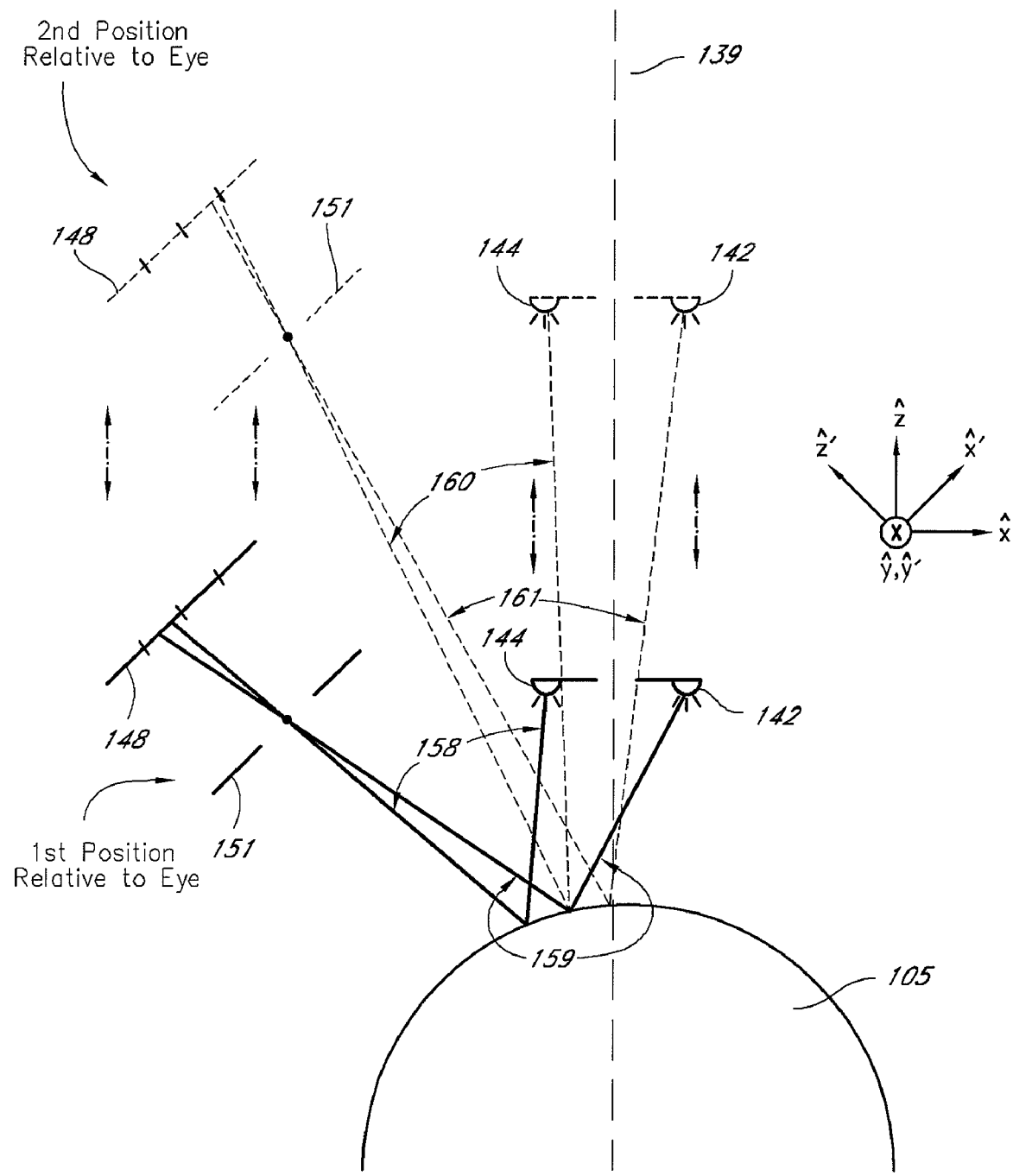
FIG. 5 schematically illustrates the translation of images of LEDs across the detector of an alignment system camera in response to longitudinal motion of the wavefront aberrometer with respect to the eye.

FIG. 5 schematically illustrates the translation of the image of the LED constellation 143 across the alignment detector 148 in response to longitudinal z-direction motion of the wavefront aberrometer 120 with respect to the eye 105. FIG. 5 uses x-y-z and x'-y'-z' coordinate systems similar to those used in FIG. 4. In the interest of simplicity, FIG. 5 illustrates only a simplified version of the alignment system 140 and excludes the wavefront aberrometer 120. The simplified alignment system 140 of FIG. 5 includes two LEDs 142, 144, the alignment system's input aperture 151, and the alignment detector 148. The alignment detector 148 is illustrated in a first position at a first longitudinal depth relative to the eye 105 using bold lines, and in a second position at a second longitudinal depth relative to the eye 105 using dashed lines.

The arrangement of the wavefront aberrometer 120 and the alignment system 140 wherein the optical axis 150 of the alignment system 140 is directed at the eye 105 at an oblique angle with respect to the optical axis 139 of the aberrometer 120 provides a high level of sensitivity in measuring longitudinal distance from the wavefront aberrometer 120 to the eye 105. In contrast, and by way of background, an imaging system arranged with its optical axis parallel to longitudinal motion of an object provides relatively imprecise information about the longitudinal distance of the object from the imaging system.

Take, for example, a simple imaging system consisting of a single positive lens and a detector. The imaging system is oriented so that its optical axis is parallel to longitudinal motion of an object. First, consider the case of an on-axis object whose longitudinal distance from the imaging system varies. As the distance of the on-axis object from the imaging system changes, the magnification and focus of the object will also change. However, depending, for example, upon the focal length and aperture size of the imaging system, these changes in magnification and focus of the object may not be sufficient to resolve small changes in distance.

Now consider the case of an off-axis object whose distance from the imaging system varies. As the longitudinal distance of the off-axis object from the imaging system changes, the magnification and focus of the image of the off-axis object will also change, as in the case of the on-axis object. Additionally, the position of the image of the off-axis object will translate across the detector. However, depending again on variables such as the focal length of the imaging system, this change may be too small to resolve small changes in distance of the off-axis object from the imaging system.

Again, the arrangement of the wavefront aberrometer 120 and the alignment system 140 wherein the optical axis 150 of the alignment system 140 is directed at the eye 105 at an oblique angle with respect to the optical axis 139 of the aberrometer 120 elegantly provides an increased level of sensitivity in measuring longitudinal distance from the wavefront aberrometer 120 to the eye 105. The oblique angle between the optical axis 139 of the aberrometer 120 and the optical axis 150 of the alignment system effectively links z-direction longitudinal motion of the wavefront aberrometer 120 with x'-direction motion of the alignment system 140 with respect to the eye 105. As described herein, imaging systems are generally more sensitive to motion of an object that is transverse to their optical axis. Since motion in the x'-direction, which is linked to z-direction longitudinal motion of the aberrometer 120, is transverse to the optical axis 150 of the alignment system, the alignment system 140 has increased sensitivity to the z-direction longitudinal position of the aberrometer 120.

For example, since the optical axis 150 of the alignment system 140 is arranged at an angle θ with respect to the optical axis 139 of the wavefront aberrometer 120, z-direction longitudinal motion of the aberrometer 120 has a vector component in the x'-direction. The alignment detector 148 senses this x'-direction component of the longitudinal motion of the wavefront aberrometer 120 as lateral motion of the eye 105 with respect to the alignment system 140. Again, the alignment system 140 generally has greater sensitivity to motion of the eye 105 in directions perpendicular to the optical axis 150 of the alignment system 140 than to motion of the eye 105 in a direction parallel to its optical axis. Thus, by interpreting z-axis longitudinal changes in the location of the wavefront aberrometer 120 as x'-direction changes in the aberrometer's position with respect to the eye 105, the alignment system 140 has increased sensitivity to longitudinal position of the aberrometer with respect to the eye 105 along the z-axis and can precisely measure small changes in z-direction longitudinal position of the aberrometer 120 with respect to the eye 105. This is illustrated by the ray-traces in FIG. 5.

FIG. 5 includes ray-traces of the images of the LEDs 142, 144 that are formed on the alignment detector 148. Rays 158 and 159 correspond to the images of LEDs 142, 144 on the alignment detector 148 when the wavefront aberrometer 120 and the alignment system 140 are in the first position at the first z-direction longitudinal position relative to the eye 105. Ray 158 is the chief ray of the image of LED 144 on the alignment detector 148. Ray 159 is the chief ray of the image of LED 142 on the alignment detector 148. Hash marks are included on the alignment detector 148 to better illustrate the distinct locations of the images of the LEDs 142, 144 on the alignment detector 148 when the wavefront aberrometer/ alignment system is at the first and second z-direction longitudinal positions, respectively. As illustrated, the images of the LEDs 142, 144 appear on the alignment detector 148 between the left and middle hash marks when the wavefront aberrometer 120 and the alignment system 140 are in the first position.

In a similar manner, rays 160 and 161 correspond to the images of LEDs 142, 144 on the alignment detector 148 when the wavefront aberrometer 120 and the alignment system 140 are in the second position at the second z-direction longitudinal position relative to the eye 105 (illustrated with dashed lines). Ray 160 is the chief ray of the image of LED 144 on the alignment detector 148. Ray 161 is the chief ray of the image of LED 142 on the alignment detector 148. As illustrated, the images of the LEDs 142, 144 move in the x'-direction in response to z-direction longitudinal motion of the wavefront aberrometer/alignment system. Consequently, the images of the LEDs 142, 144 are located near the right hash mark of the alignment detector 148 when the wavefront aberrometer 120 and the alignment system 140 are in the second position at the second z-direction longitudinal position relative to the eye 105. In this way, the location of the image of the LED constellation 143 on the alignment detector 148 also provides information about the z-direction longitudinal coordinate of the wavefront aberrometer 120 with respect to the patient's eye 105.

The sensitivity of the alignment system 140 to z-direction longitudinal motion of the wavefront aberrometer 120 depends upon several variables. For example, the pixel pitch of the alignment detector can be increased in order to resolve smaller changes in z-direction longitudinal position of the wavefront aberrometer 120. In some embodiments, the pixel pitch of the alignment detector is at least about 150-250 pixels per mm, though greater or lesser pixel pitches could also be used in some embodiments. In some embodiments, the pixel pitch of the alignment detector is approximately 180 pixels per mm. Also, the focal length of the alignment system optics 146 can be changed to widen or narrow the field-of-view of the alignment system, thus altering the unit change in the x'-direction location of the image of the LED constellation 143 on the alignment detector 148 per unit displacement in the z-direction longitudinal location of the wavefront aberrometer 120. The angle θ can also be varied to alter the x'-direction component of z-direction longitudinal motion of the aberrometer 120 and, hence, the unit change in the x'-direction location of the image of the LED constellation 143 on the alignment detector 148 per unit displacement in the z-direction longitudinal location of the wavefront aberrometer 120. In some embodiments, the alignment system 140 allows for longitudinal positioning of the wavefront aberrometer with enough accuracy to achieve less than 0.15 D worth of error for refraction values up to +25 D (e.g., as illustrated on plot 100 of FIG. 1).

While orientation of the optical axis 150 of the alignment system 140 at an angle θ with respect to the optical axis 139 of the wavefront aberrometer 120 is one way of coupling z-direction longitudinal motion of the aberrometer 120 with x'-direction transverse motion of the alignment system 140 with respect to the eye 105, other configurations that perform this function are also possible and may be used in some embodiments. For instance, in some embodiments, the LEDs 142, 144 are positioned off-axis from the optical axis 139 of the aberrometer 120 while the alignment camera is placed on-axis.

As described herein, the location of the image of the LED constellation 143 on the alignment detector 148 changes in response to x-y-direction lateral motion, as well as z-direction longitudinal motion, of the wavefront aberrometer 120 with respect to the eye 105. As also described herein, it is desirable for the wavefront aberrometer 120 to be precisely positioned with respect to the corneal apex of a patient's eye 105 in order to obtain the best measurement results, and consequently, the best surgical outcome for the patient. When the wavefront aberrometer 120 is located at the desired position with respect to the corneal apex of the eye 105, the center of the image of the LED constellation 143 on the alignment detector 148 will be located at a specific corresponding point on the alignment detector 148. In some embodiments, this reference point on the alignment detector 148 can be designated by, for example, a crosshair 162 (see, e.g., FIG. 6). Thus, the wavefront aberrometer 120 is located at the desired position with respect to the corneal apex of the eye 105 when the image of the LED constellation 143 on the alignment detector 148 has a predetermined spatial relationship relative to the crosshair 162 on the alignment detector 148. This is illustrated in greater detail in FIGS. 6-8.

The location of the crosshair 162 on the alignment detector 148 will vary in response to several parameters. First, the location of the crosshair 162 will vary based on the desired position of the wavefront aberrometer 120 (e.g., the desired x,y,z coordinates of the aberrometer) with respect to the corneal apex of the eye 105, or other target location. The location of the crosshair 162 will also vary in response to the corneal curvature, asphericity, and differences in local topography of the patient's eye 105. Based on these and perhaps other parameters, such as calibration data for the alignment system 140, the location of the crosshair 162 on the alignment detector 148 can be determined. The cross hair location may, for example, correspond to the location of the center of the LED constellation image 143 (e.g., the centroid of the constellation image) on the alignment detector 148 when the wavefront aberrometer 120 is located at the desired position relative to the eye.

In some embodiments, the location of the crosshair 162 is calculated by, for example, the processor 136 based on the foregoing parameters (e.g., corneal curvature, the desired spatial position of the wavefront aberrometer 120 relative to the corneal apex of the eye 105, calibration data, etc.) using ray-tracing or other computational methods. In some embodiments, the location of the crosshair 162 may be measured, using, for example, one or more calibrated reflective balls, or calculated using an external processor. The locations of the crosshair 162 for several different corneal curvatures can then be stored in a lookup table in the memory 138 (crosshair locations for corneal curvatures between the discrete values stored in the lookup table can be determined by interpolation). The proper crosshair 162 location can be retrieved from the memory 138, and the crosshair 162 properly positioned on the video monitor 137, in response to data entry of the corneal curvature of a patient's eye by the surgeon.

FIGS. 6-12 illustrate a method for positioning an optical instrument 120, such as a wavefront aberrometer, at a desired spatial position relative to a target location 119, such as the corneal apex of a patient's eye 105, using the alignment system 140. In one embodiment, the alignment process begins by immobilizing the patient's head on, for example, an operating table. The surgeon may have used any appropriate instrument to measure the corneal curvature of the patient's eye 105. For example, the corneal curvature may be represented by two values, K1 and K2, which represent the curvature of the patient's cornea in two orthogonal planes that intersect the eye 105. The surgeon can then enter this corneal curvature data into the memory 138 of the alignment system 140, and the processor 136 can use this corneal curvature data, along with knowledge of the proper working distance for the wavefront aberrometer 120, to determine the location of the crosshair 162 on the alignment detector 148.

Having been restrained, the patient is instructed to fixate his vision on a light that is positioned so as to attempt to cause the patient to orient his eye so as to align its visual axis with the optical axis 139 of the wavefront aberrometer 120. Next, the surgeon may begin the process of coarsely laterally centering the wavefront aberrometer over the corneal apex of the patient's eye 105. This may be done in part by using the surgical microscope 110 to center a reticle marking within the microscope's field of view over the patient's pupil. The surgeon may also use the surgical microscope 110 to coarsely longitudinally position the optical instrument 120 with respect to the patient's eye 105 by focusing the microscope on the corneal apex. The surgeon may then turn to the alignment system 140 for further alignment of the wavefront aberrometer 120 with respect to the corneal apex of the patient's eye 105.

Figure 6:
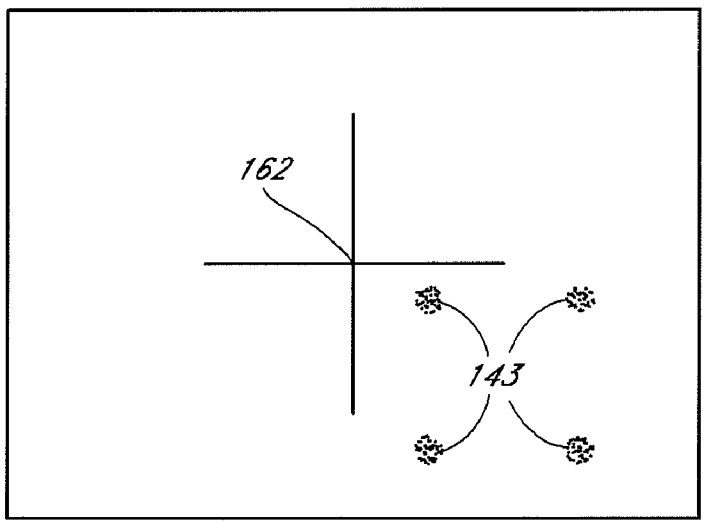
FIG. 6 is an example image produced by an alignment system camera that is used during the wavefront aberrometer alignment process.
Figure 6:
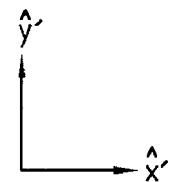

FIG. 6 is an example image produced at the alignment detector 148 during the wavefront aberrometer 120 alignment process. As described herein, in some embodiments video data from the alignment detector 148 is outputted to a video monitor 137 or other display. FIG. 6 may, for example, represent a screenshot from the video monitor 137. As illustrated in FIG. 6, the crosshair 162 is imposed upon the video data from the alignment detector 148. Again, the position of the crosshair 162 may be determined based at least in part on the corneal curvature of the patient's eye 105.

The surgeon moves the wavefront aberrometer 120 in three dimensions until the wavefront aberrometer 120 is at the desired position relative to the corneal apex of the patient's eye 105 to achieve accurate measurements of the refractive power of the patient's eye 105. In some embodiments, the surgeon does this by viewing the video signal on the video monitor 137 and moving the wavefront aberrometer 120 to achieve a desired relative spatial position between the image of the constellation of LEDs 143 and the crosshair 162. In some embodiments, the desired relative spatial position between the image of the constellation of LEDs 143 and the crosshair 162 corresponds to centering the constellation image 143 on the crosshair 162. In the screenshot illustrated in FIG. 6, it is evident that the constellation image 143 should be adjusted in both the x'-direction and in the y'-direction.

Figure 7:
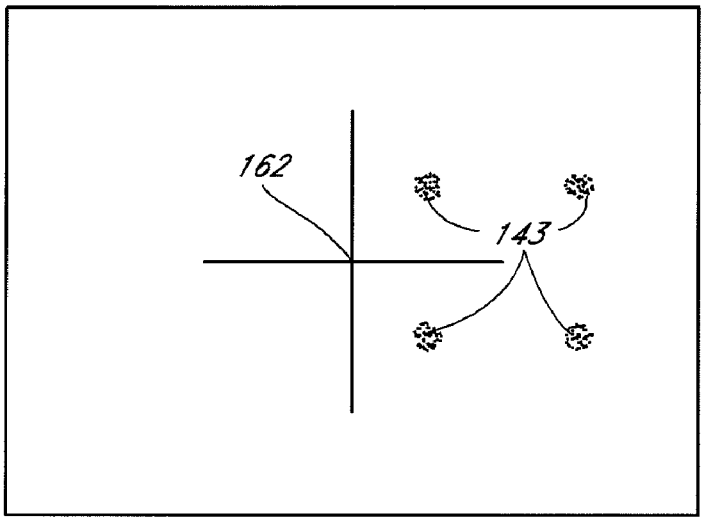
FIG. 7 is an example image produced by the alignment system camera that is used during the wavefront aberrometer alignment process after the aberrometer has been partially laterally aligned with respect to the eye.
Figure 7:
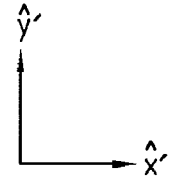

FIG. 7 is an example image produced at the alignment detector 148 during the wavefront aberrometer 120 alignment process after the aberrometer has been partially laterally aligned. Specifically, FIG. 7 schematically illustrates that the wavefront aberrometer 120 has been aligned in the y-direction. The surgeon aligns the wavefront aberrometer 120 in the y-direction by moving it until the LED constellation image 143 is appropriately centered on the alignment detector 148 in the y'-direction, as illustrated in FIG. 7. In the embodiments illustrated in FIGS. 3-5, motion of the LED constellation image 143 on the alignment detector in the y'-direction corresponds to motion of the wavefront aberrometer in the y-direction.

Having been properly aligned in the y-direction, the wavefront aberrometer 120 is next aligned in the x-direction and in the z-direction. As described herein, the location of the image of the LED constellation 143 on the alignment detector 148 changes in the x'-direction in response to both x-direction and z-direction motion of the wavefront aberrometer 120 with respect to the eye 105. This is due to the fact that both x-direction and z-direction motion each have a vector component in the x'-direction. This x'-direction component of motion is sensed by the alignment detector 148 as x'-direction motion of the image of the LED constellation 143 on the alignment detector 148. Since both x-direction and z-direction motion result in x'-direction motion of the image of the LED constellation 143 on the alignment detector 148, there is a continuous range of (x,y,z) spatial coordinates of the wavefront aberrometer that correspond to the image of the LED constellation 143 having the desired spatial relationship with respect to the crosshair 162.

Despite this ambiguity, the correct set of (x,y,z) spatial coordinates (that correspond to the desired spatial position of the wavefront aberrometer 120 with respect to the corneal apex of the eye 105) can be selected based on additional information about the spot size of the image of each individual LED in the LED constellation 143 on the alignment detector 148 and the sharpness of focus of the spots. For example, the spot size/sharpness of each individual LED will change as the alignment system 140 is moved nearer or further from the eye 105 because the images of the LEDs will be more or less in focus.

In one embodiment, the alignment optics 148 are designed so that the images of the individual LEDs in the LED constellation 143 will be focused to the greatest degree when the wavefront aberrometer 120 is positioned so that its depth from the corneal apex of the eye 105 is equal to the desired working distance of the aberrometer. Thus, the spot sizes of the images of the individual LEDs in the LED constellation on the alignment detector 148 will be minimized, and the sharpness of focus of the spots enhanced, when the wavefront aberrometer 120 is positioned at the desired z-direction depth from the corneal apex of the eye 105. As a result, the iterative movement of the wavefront aberrometer 120 by, for example, a surgeon so that the image of the LED constellation 143 on the alignment detector 148 has the desired spatial relationship relative to the crosshair 162, and so that the spot sizes of the images of the LEDs are simultaneously minimized (and the sharpness of the spots is enhanced), results in the wavefront aberrometer 120 being generally located at the desired spatial position relative to the corneal apex of the eye 105.

Figure 8:
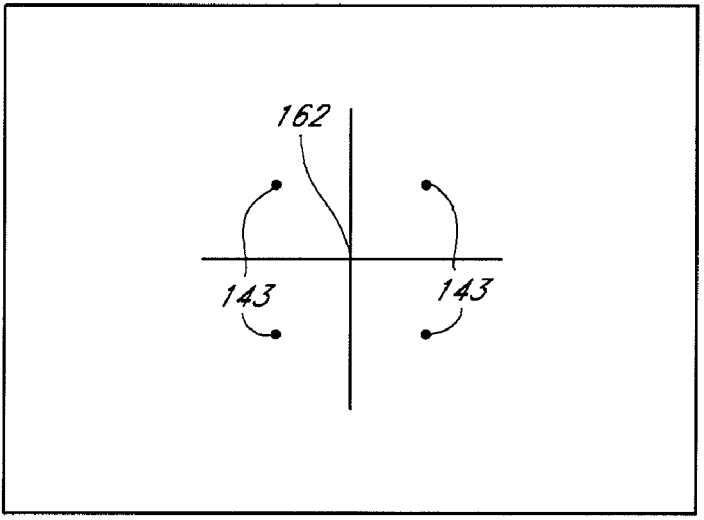
FIG. 8 is an example image produced by the alignment system camera that is used during the wavefront aberrometer alignment process after the aberrometer has been aligned both laterally and longitudinally with respect to the eye.
Figure 8:
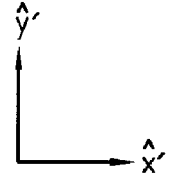

FIG. 8 is an example image produced at the alignment detector 148 during the wavefront aberrometer 120 alignment process after the aberrometer has been coarsely aligned both laterally and longitudinally. As illustrated in FIG. 8, the LED constellation image 143 is not only substantially centered on the crosshair 162, but the spot sizes of the individual LED images have been reduced and the focus enhanced, as compared to the spot sizes in FIGS. 6 and 7. In some embodiments, the simultaneous minimization of the LED spot sizes, along with achievement of the desired spatial relationship between the crosshair 162 and the LED constellation image 143 (e.g., centering the LED constellation image on the crosshair), corresponds to the wavefront aberrometer 120 being properly coarsely aligned with the corneal apex of the patient's eye 105 both laterally and longitudinally.

The state of lateral and longitudinal alignment of the wavefront aberrometer achieved in FIG. 8 is coarse because it is based on the surgeon's perception of the LED constellation image 143 being properly centered on the crosshair 162 and having minimal spot sizes. In some embodiments, such coarse lateral and longitudinal alignment may be sufficient. However, in other embodiments, the wavefront aberrometer 120 and the alignment system 140 can be used to more finely align the instrument with respect to the patient's corneal apex. For example, in some embodiments, the surgeon may finely laterally center the wavefront aberrometer 120 over the patient's corneal apex using images provided by the aberrometer detector 134. To do this, the surgeon may cause the processor 136 to change the video display to video data from the aberrometer detector 134.

Figure 9:
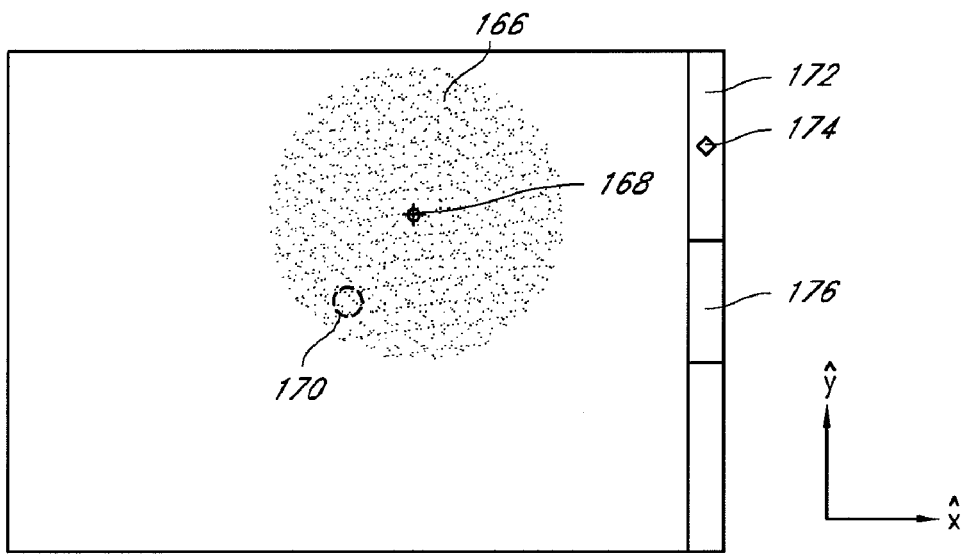
FIG. 9 is an example image produced by the wavefront aberrometer during the alignment process and after the aberrometer has been coarsely laterally aligned with respect to the eye.

FIG. 9 is an example image produced at the aberrometer detector 134 during the wavefront aberrometer 120 alignment process after the aberrometer has been coarsely laterally and longitudinally aligned. FIG. 9 includes an image of the laser beam spot 166 formed on the aberrometer detector 134 by the laser 122. FIG. 9 also includes a crosshair 168 that corresponds to the center of the pattern 166 generated by the aberrometer. In addition, the wavefront aberrometer includes an internal centering reticle marking 170, as illustrated in FIG. 9. For example, the centering reticle 170 may mark the intersection of the optical axis 139 of the wavefront aberrometer 120 with the aberrometer detector 134 therein. Based on the video signal from the aberrometer detector 134, the surgeon can move the wavefront aberrometer 120 in the x-direction and in the y-direction with respect to the corneal apex of the patient's eye 105. In some embodiments, this is done by centering the crosshair 168 in the centering reticle 170 of the wavefront aberrometer 120. As illustrated in FIG. 9, the wavefront aberrometer 120 is not finely laterally centered with respect to the corneal apex because the pattern 166 generated by the aberrometer is not centered on the centering reticle 170.

Figure 10:
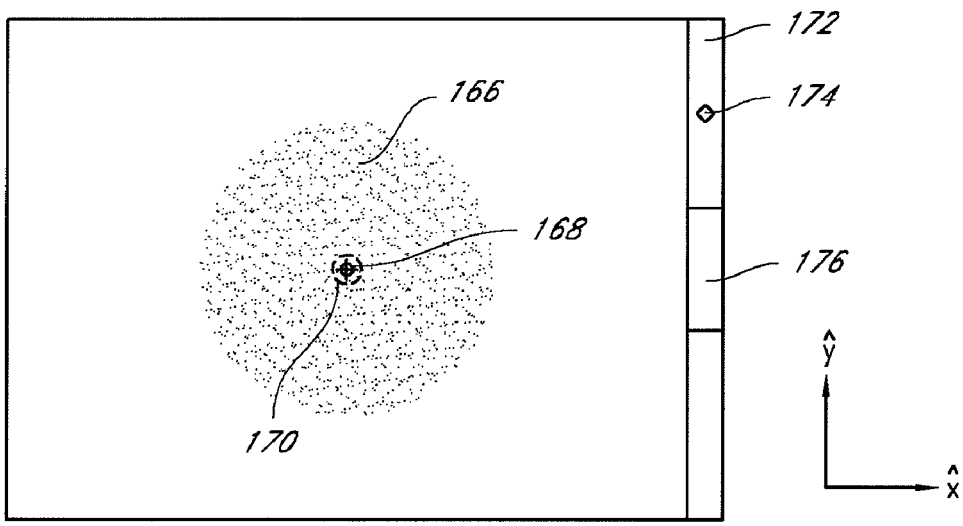
FIG. 10 is an example image produced by the wavefront aberrometer during the alignment process and after the aberrometer has been coarsely longitudinally aligned, and finely laterally aligned with respect to the eye.

FIG. 10 is an example image produced at the aberrometer detector 134 during the wavefront aberrometer 120 alignment process after the aberrometer has been coarsely aligned longitudinally, and finely laterally aligned. As illustrated in FIG. 10, the crosshair 168 has been located within the centering reticle 170 of the wavefront aberrometer 120. Thus, the wavefront aberrometer 120 is finely laterally aligned relative to the corneal apex of the eye 105.

Once the surgeon has finely aligned the wavefront aberrometer to the corneal apex in the x-direction and in the y-direction, the surgeon may finely align the instrument longitudinally (i.e. in the z-direction). As discussed herein, once the beam spot sizes of the LED images are minimized on the alignment detector 148, and the sharpness of the images is enhanced, while the LED constellation image 143 is simultaneously centered on the crosshair 162, the wavefront aberrometer is coarsely aligned in the x-direction, the y-direction, and the z-direction. This lateral and longitudinal alignment of the wavefront aberrometer 120 is coarse because it depends upon the perception of the surgeon. However, once the instrument is finely laterally aligned using the wavefront aberrometer's centering reticle 170, the alignment system can accurately determine the magnitude of any remaining longitudinal positioning error. This can be done by using the processor 136 to calculate the center point of the LED constellation image 143, and to then determine the distance between the center point of the LED constellation image 143 and the crosshair 162.

Since the wavefront aberrometer 120 is finely laterally aligned, any remaining appreciable offset between the center of the LED constellation image 143 and the crosshair 162 is likely to be the result of longitudinal alignment error. In some embodiments, the processor 136 determines the center point of the LED constellation image 143 by calculating the centroid of the constellation image 143. The magnitude of the distance between the centroid of the LED constellation 143 and the crosshair 162 depends on the magnitude of longitudinal alignment error. In some embodiments, the magnitude of this longitudinal alignment error is displayed to the surgeon who then moves the wavefront aberrometer in the z-direction until the longitudinal alignment error is within an acceptable tolerance.

FIG. 10 includes a longitudinal alignment indicator bar 172 having a longitudinal alignment target zone 176, and a longitudinal alignment indicator 174. The position of the longitudinal alignment indicator 174 on the indicator bar 172 illustrates whether fine longitudinal alignment has been achieved. In particular, once the longitudinal alignment indicator 174 is positioned within the longitudinal alignment target zone 176, the wavefront aberrometer 120 is positioned such that its depth is within an acceptable tolerance of the aberrometer's proper working distance from the corneal apex. Once the wavefront aberrometer 120 is properly aligned, both laterally and longitudinally, it may begin acquisition of wavefront measurements. As illustrated in FIG. 10, the longitudinal alignment indicator 174 is well outside the longitudinal alignment target zone 176, indicating an unacceptable amount of longitudinal alignment error.

Figure 11:
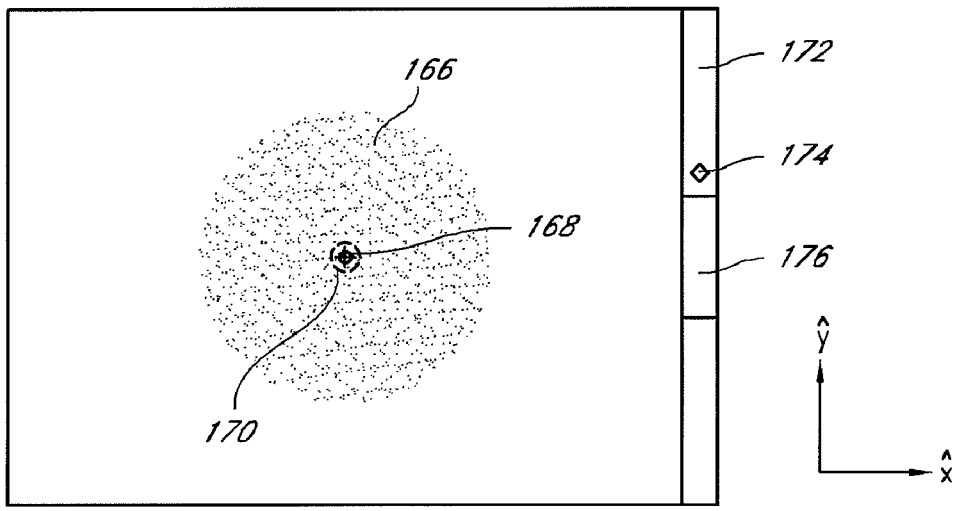
FIG. 11 is an example image produced by the wavefront aberrometer during fine alignment of the longitudinal position of the wavefront aberrometer with respect to the eye.

FIG. 11 is an example image produced at the aberrometer detector 134 during fine alignment of the longitudinal position of the wavefront aberrometer 120. As illustrated in FIG. 11, the longitudinal alignment indicator 174 is just outside the longitudinal alignment target zone 176 on the longitudinal alignment indicator bar 172. This corresponds to the surgeon having adjusted the longitudinal positioning of the wavefront aberrometer somewhat in response to the longitudinal alignment indicator 174, when compared to the position of the longitudinal alignment indicator 174 in FIG. 10.

Figure 12:
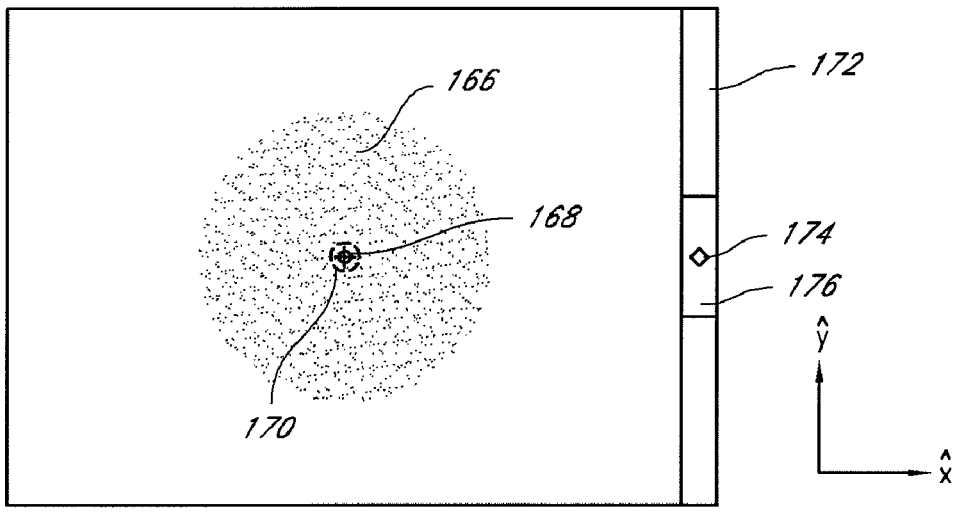
FIG. 12 is an example image produced by the wavefront aberrometer after achieving both fine lateral and longitudinal alignment of the wavefront aberrometer with respect to the eye.

FIG. 12 is an example image produced at the aberrometer detector 134 after achieving both fine lateral and longitudinal alignment of the wavefront aberrometer 120. As illustrated in FIG. 12, the longitudinal alignment indicator 174 is now within the longitudinal alignment target zone 176 on the longitudinal alignment indicator bar 172. This corresponds to the surgeon having adjusted the longitudinal positioning of the wavefront aberrometer to the proper working distance from the corneal apex of the patient's eye in response to the longitudinal alignment indicator 174.

In some embodiments, once fine lateral and longitudinal alignment of the wavefront aberrometer 120 have been achieved, the wavefront aberrometer 120 begins acquisition of wavefront measurement data. If the alignment of the aberrometer 120 is upset beyond certain tolerance levels (e.g., the longitudinal alignment indicator 174 goes outside the longitudinal alignment target zone 176 or the laser beam crosshair 168 goes outside the centering reticle 170) at any point during acquisition of the wavefront data, the acquisition process may be interrupted until the surgeon once again establishes proper alignment of the instrument with respect to the corneal apex of the patient's eye 105. Data may only be captured and/or used when the wavefront aberrometer 120 is properly positioned with respect to the eye 105 within certain tolerance levels. For example, the tolerance level for lateral alignment may be 3 mm or less (with a typical value of 1 mm or less), while the tolerance level for longitudinal alignment may be 4 mm or less (with a typical value of 1 mm or less).

In some embodiments, the longitudinal alignment error in the position of the wavefront aberrometer 120 relative to the corneal apex of the eye 105 is continuously monitored. The processor 136 can do this, for example, by continuously tracking the distance on the alignment detector 148 between the calculated center of the LED constellation image 143 and the crosshair 162. These longitudinal positioning error values can be used to improve the accuracy of the refractive power measurements by vertex correction of any longitudinal positioning errors back to the corneal apex.

For example, the desired longitudinal position of the wavefront aberrometer 120 with respect to the eye 105 may correspond to the aberrometer being positioned at a z-coordinate, $z_0$. In practice, the wavefront aberrometer 120 may be positioned at $z_0 \pm \Delta z$, where $\Delta z$ represents longitudinal positioning error. In some embodiments, longitudinal positioning error, $\Delta z$, is continuously tracked and fed into the vertex correction calculations to improve their accuracy.

Preferred embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, a wide variety of variation is possible. Components, and/or elements may be added, removed, or rearranged. Additionally, processing steps may be added, removed, or reordered. Various algorithms that have been described herein can be performed in software, hardware, or a combination of the two.

While certain embodiments have been explicitly described, other embodiments will become apparent to those of ordinary skill in the art based on this disclosure. Therefore, the scope of the invention is intended to be defined by reference to the claims and not simply with regard to the explicitly described embodiments.

What is claimed is:

1. An ophthalmic apparatus, comprising:
an optical instrument having a first set of optics configured to receive light from the eye of a patient along a first optical axis defined by the first set of optics; and
a system for positioning the optical instrument with respect to a desired position relative to the eye in an x-y-z three-dimensional coordinate system, the desired position comprising x, y, and z coordinates, the positioning system comprising a photodetector and being calibrated to define a reference location on the photodetector, the reference location on the photodetector being determined based at least in part on the corneal curvature of the eye and on the desired position relative to the eye, the apparatus being configured such that a spatial relationship between at least one optical indicia and the reference location on the photodetector varies as the apparatus is moved relative to the eye to provide x-y-z three-dimensional positioning information for positioning the instrument with respect to the desired position, the optical indicia comprising light reflected from the eye to the photodetector along a second optical axis, different from the first.

2. The ophthalmic apparatus of claim 1, wherein the optical instrument comprises a diagnostic instrument.

3. The ophthalmic apparatus of claim 2, wherein the optical instrument is configured to measure refractive power of the eye.

4. The ophthalmic apparatus of claim 3, wherein the optical instrument comprises a wavefront sensor.

5. The ophthalmic apparatus of claim 1, further comprising actuators to move the optical instrument relative to the eye.

6. The ophthalmic apparatus of claim 1, wherein the positioning system further comprises a second set of optics that define the second optical axis, and wherein the first optical axis and the second optical axis are not parallel.

7. The ophthalmic apparatus of claim 6, wherein the first optical axis and the second optical axis intersect.

8. The ophthalmic apparatus of claim 7, wherein the first optical axis and the second optical axis intersect at a point substantially at the corneal apex of the eye when the optical instrument is positioned at the desired position.

9. The ophthalmic apparatus of claim 8, wherein the angle between the first optical axis and the second optical axis is in the range from approximately 10 degrees to approximately 15 degrees.

10. The ophthalmic apparatus of claim 6, wherein the second set of optics has a focal length in the range from approximately 10 millimeters to approximately 40 millimeters.

11. The ophthalmic apparatus of claim 1, wherein the photodetector comprises a two dimensional array of pixels, and wherein the pitch of the pixels is in the range from approximately 150 pixels per millimeter to approximately 250 pixels per millimeter.

12. The ophthalmic apparatus of claim 1, wherein the at least one optical indicia comprises light from a light source fixedly mounted to the optical instrument.

13. The ophthalmic apparatus of claim 12, wherein the at least one optical indicia comprises light from a plurality of light sources arranged about the first optical axis.

14. The ophthalmic apparatus of claim 13, wherein the at least one optical indicia comprises an image of the plurality of light sources on the photodetector and wherein the centroid of the imaged plurality of light sources is coincident with the reference location on the photodetector when the optical instrument is located at the desired position relative to the eye.

15. The ophthalmic apparatus of claim 14, wherein the image of the plurality of light sources on the photodetector is substantially in focus when the optical instrument is located at the desired position relative to the eye.

16. The ophthalmic apparatus of claim 1, wherein a predetermined spatial relationship between the at least one optical indicia and the reference location on the photodetector corresponds to the instrument being positioned at the desired position relative to the eye.

17. The ophthalmic apparatus of claim 1, wherein the desired position relative to the eye corresponds to the first optical axis substantially normally intersecting the corneal apex of the eye.

18. The ophthalmic apparatus of claim 17, wherein the desired position relative to the eye corresponds to the instrument being located at a predetermined distance from the corneal apex.

19. The ophthalmic apparatus of claim 1, wherein the spatial relationship between the at least one optical indicia and the reference location on the photodetector comprises the positioning information, and further comprising a display for providing a visual representation of said spatial relationship.

20. The ophthalmic apparatus of claim 1, further comprising a two-dimensional x'-y' coordinate system that is coplanar with the photodetector, wherein the positioning system is configured to encode information about the position of the optical instrument in the three-dimensional coordinate system into information in the two-dimensional coordinate system that is detectable by the photodetector.

21. The ophthalmic apparatus of claim 20, wherein:
the three-dimensional x-y-z coordinate system comprises:
a z-axis parallel to the first optical axis;
a y-axis orthogonal to the z-axis and parallel to the plane of the photodetector; and
an x-axis orthogonal to the y and z axes; and
the two-dimensional x'-y' coordinate system comprises:
a y'-axis parallel to the y-axis; and
an x'-axis orthogonal to the y'-axis,
wherein movement of the optical instrument in the direction of the y-axis corresponds to movement of the location of the at least one optical indicia in the direction of the y'-axis, and wherein movement of the optical instrument in the direction of the x-axis or the z-axis corresponds to movement of the location of the optical indicia in the direction of the x'-axis.

22. The ophthalmic apparatus of claim 21, wherein ambiguity related to movement of the optical indicia in the direction of the x'-axis, which corresponds to movement of the optical instrument in either the x-axis or the z-axis, is resolved by the spot size and sharpness of the at least one optical indicia on the photodetector.

23. The ophthalmic apparatus of claim 4, wherein the wavefront sensor comprises a Talbot-Moiré interferometer.

24. The ophthalmic apparatus of claim 1, wherein the apparatus is configured to monitor a longitudinal positioning error value while the optical instrument performs a measurement, the longitudinal positioning error value comprising the difference between a longitudinal coordinate of the desired position and an actual longitudinal position of the eye relative to the optical instrument.

25. The ophthalmic apparatus of claim 24, wherein the measurement comprises a measurement of the refractive power of the eye, and wherein the apparatus is configured to use the longitudinal positioning error value in a calculation to improve the accuracy of the refractive power measurement.

26. The ophthalmic apparatus of claim 25, wherein the apparatus is configured to use the longitudinal positioning error value to improve the accuracy of the refractive power measurement by using the longitudinal positioning error value in a vertex correction calculation corresponding to the refractive power measurement.

27. An ophthalmic apparatus, comprising:
an optical instrument having a first set of optics configured to receive light from the eye of a patient along a first optical axis defined by the first set of optics; and
a system for positioning the optical instrument with respect to a desired position relative to the eye in an x-y-z three-dimensional coordinate system, the desired position comprising x, y, and z coordinates, the positioning system comprising a photodetector and being calibrated to define a reference location on the photodetector, the reference location on the photodetector being determined based at least in part on a measurement of the corneal curvature of the eye of the patient and on the desired position relative to the eye, the apparatus being configured such that a spatial relationship between at least one optical indicia and the reference location on the photodetector varies as the apparatus is moved relative to the eye to provide positioning information for positioning the instrument with respect to the desired position, the optical indicia comprising light reflected from the eye to the photodetector along a second optical axis, different from the first.

28. The ophthalmic apparatus of claim 27, wherein the optical instrument is configured to measure refractive power of the eye.

29. The ophthalmic apparatus of claim 27, wherein the first optical axis and the second optical axis intersect at a point substantially at the corneal apex of the eye when the optical instrument is positioned at the desired position.

30. The ophthalmic apparatus of claim 27, wherein the apparatus is configured to monitor a longitudinal positioning error value while the optical instrument performs a measurement of refractive power of the eye, the longitudinal positioning error value comprising the difference between a longitudinal coordinate of the desired position and an actual longitudinal position of the eye relative to the optical instrument, and wherein the apparatus is configured to use the longitudinal positioning error value to improve the accuracy of the refractive power measurement by using the longitudinal positioning error value in a vertex correction calculation corresponding to the refractive power measurement.

31. An ophthalmic apparatus, comprising:
an optical instrument having a first set of optics configured to receive light from the eye of a patient along a first optical axis defined by the first set of optics; and
a system for positioning the optical instrument with respect to a desired position relative to the eye in an x-y-z three-dimensional coordinate system, the desired position comprising x, y, and z coordinates, the positioning system comprising a photodetector and being calibrated to define a reference location on the photodetector, the reference location on the photodetector being determined based at least in part on the corneal curvature of the eye and on the desired position relative to the eye, the apparatus being configured such that a spatial relationship between at least one optical indicia and the reference location on the photodetector varies as the apparatus is moved relative to the eye to provide positioning information for positioning the instrument with respect to the desired position, the optical indicia comprising light from at least one light source arranged about the first optical axis and reflected from the eye to the photodetector along a second optical axis, different from the first, the light source being positioned such that the light from the light source reflects to the photodetector from a location offset from the corneal apex when the optical instrument is located at the desired position relative to the eye.

32. The ophthalmic apparatus of claim 31, wherein the optical instrument is configured to measure refractive power of the eye.

33. The ophthalmic apparatus of claim 31, wherein the apparatus is configured to monitor a longitudinal positioning error value while the optical instrument performs a measurement of refractive power of the eye, the longitudinal positioning error value comprising the difference between a longitudinal coordinate of the desired position and an actual longitudinal position of the eye relative to the optical instrument, and wherein the apparatus is configured to use the longitudinal positioning error value to improve the accuracy of the refractive power measurement by using the longitudinal positioning error value in a vertex correction calculation corresponding to the refractive power measurement.

* * * * *